United States Patent [19]

Jalics

[11] 3,959,398

[45] May 25, 1976

[54] ALPHA-METHYL-P-BROMO-STYRENE AND METHOD OF PREPARATION

[75] Inventor: George Jalics, Akron, Ohio

[73] Assignee: The Goodyear Tire & Rubber Company, Akron, Ohio

[22] Filed: June 3, 1974

[21] Appl. No.: 475,711

[52] U.S. Cl............................. 260/650 R; 526/12; 526/14; 526/17; 526/19; 526/43; 526/914; 526/237; 526/206; 526/72; 526/240; 526/274; 526/296; 526/297; 526/318; 526/321; 526/335; 526/343; 526/344; 526/346; 526/348
[51] Int. Cl.² ...................................... C07C 17/02
[58] Field of Search.......... 260/91.5, 93.5 A, 650 R; 450/616.5, 617, 765

[56] References Cited
UNITED STATES PATENTS

| 2,443,217 | 6/1948 | Amos et al............................ 260/669 |
| 2,732,371 | 1/1956 | Wehr et al........................... 260/93.5 |
| 3,009,906 | 11/1961 | Eichhorn et al.................... 260/93.5 |
| 3,770,668 | 11/1973 | Corbett et al...................... 260/2.5 E |

Primary Examiner—Stanford M. Levin
Attorney, Agent, or Firm—F. W. Brunner; H. C. Young, Jr.

[57] ABSTRACT

Alpha-methyl-p-bromo-styrene prepared by the manipulative steps of brominating poly($\alpha$-methylstyrene) and subsequently depolymerizing the brominated polymer. The alpha-methyl-p-bromo-styrene has particular utility as a co-monomer for preparing copolymers exhibiting a flame retardancy.

5 Claims, No Drawings

ALPHA-METHYL-P-BROMO-STYRENE AND METHOD OF PREPARATION

This invention relates to a bromine containing hydrocarbon, to its method of preparation, and to its copolymer with other reactive materials. This invention particularly relates to a fire retardancy conveying compound and to its incorporation into polymers.

Fire retardancy is becoming an increasingly desired property of various polymers. Many polymeric compositions which presently have acceptable flammability limits may not be acceptable at future times. Therefore, improved methods of imparting flame retardants to polymeric materials is continually sought.

Generally, the flammability of organic polymers has been reduced by the addition of inorganic materials, organometallic materials and halogen containing polymers by mixing with the polymer or copolymerization therewith.

Compounding, or mixing, of materials with the polymers can generally be the simplest method. However, the flame retardant additives do not generally form chemical bonds with the organic polymer and consequently act primarily as fillers with the corresponding dilution or sacrifice of the polymer's physical properties.

Copolymerization of the flame retardant materials with the organic monomers, on the other hand, can provide the advantage expected of polymerizable monomers which become chemically bound into the polymer chain itself. Thus, it can be possible that the physical properties of the resulting polymer are actually improved while obtaining the beneficial flame retardancy.

Many bromine containing compounds are known to be useful as flame retardants. As additives they are useful to render polymers less flammable. Polymers have also been made less flammable by halogen incorporation into the polymer by copolymerization with halogen containing monomers. Examples of such monomers are chloro and bromostyrenes. The latter can be prepared by brominating polystyrene and then thermally decomposing polybromostyrene into its monomer. This monomer in turn can be copolymerized with other monomers to produce a non-flammable polymer with the desired physical properties. However, the yield for the depolymerization reaction is low, and produces other fragments besides the desired monomer.

This invention circumvents this problem by providing a bromopolymer which, it has been discovered, can be decomposed in good yield into its monomeric form.

In accordance with this invention, $\alpha$-methyl-p-bromo-styrene is provided as a flame retardant monomer as well as a unique method for its preparation and various copolymers thereof.

In the practice of this invention, $\alpha$-methyl-p-bromo-styrene is prepared by the method which comprises the manipulative steps of brominating poly($\alpha$-methyl-styrene) and subsequently depolymerizing the brominated polymer. In particular, the method comprises obtaining an organic solvent solution of poly($\alpha$-methyl-styrene) having a molecular weight in the range of about 1000 to about 200,000 and brominating said polymer at a temperature in the range of about 20° to about 100°C with liquid or gaseous bromine and subsequently depolymerizing said brominated polymer while essentially simultaneously recovering the product as a distillate by heating said solution to a temperature in the range of about 250° to about 500°C, preferably about 300° to about 400°C. Generally a reduced pressure of about 1 to about 500, preferably about 5 to about 200, millimeters of mercury is used. Preferably, the depolymerization step is conducted by essentially instantaneously heating said polymer solution to the required temperature over a period of about 0.1 second to about 2 minutes.

The depolymerized polymer can be refined by distillation to a temperature of about 60° to about 90°C at a reduced pressure of about 0.1 to about 500, preferably about 5 to about 200, millimeters of mercury to provide a distillate having a melting point of about 12° to about 18°C, as determined by heating in a capillary tube at about 1°C per minute. The distillate is typically further characterized by a boiling point of about 80° to about 85°C, at about 7 millimeters of mercury, a density of about 1.34 to about 1.35 at 25°C and a refractive index of about 1.579 to about 1.580 at 25°C.

Generally, it is desired to mix with the depolymerized brominated polymer a weak base, such as aluminum oxide or magnesium oxide to simply scavenge or destroy possible residual Lewis acids which might have been used to prepare the original polymer which could potentially repolymerize the new monomer cationically during the fractionation recovery step.

The $\alpha$-methyl-p-bromo-styrene monomer of this invention can be used to enhance flame retardancy of various polymers by free radical addition solution or emulsion polymerization with various vinyl polymerizable double bond compounds. Such reactions are generally conducted with the aid of well-known free radical initiators such as the various peroxides, hydroperoxides, azo compounds as well as redox systems for emulsion polymerizations. Representative of the many and various vinyl polymerizable double bond compounds are dienes containing 4 to 6 carbon atoms such as 1,3-butadiene, isoprene, dimethyl butadiene and piperylene; monoolefins containing 2 to 4 carbon atoms such as ethylene, propylene and isobutylene; vinyl aromatic compounds such as styrene, chlorostyrene, vinyl toluene, $\alpha$-methyl styrene and divinyl benzene; monobasic acid esters such as alkyl ($C_1$ to $C_{10}$) and alkoxy ($C_1$–$C_4$) acrylates and methacrylates, especially methyl methacrylate; dibasic acid esters such as maleate, fumarate and itaconate; vinyl cyanides such as acrylonitrile and methacrylonitrile; vinyl chloride; vinylidene chloride; vinyl ethers such as methyl vinyl ether; vinyl esters such as vinyl acetate and esters of $C_8$–$C_{10}$ acids; vinyl phophonates; organophosphates such as mono, di and tri allyl phosphates; vinyl silanes; and vinyl antimonies such as antimony fumarate. Particularly exemplary of aqueous emulsion polymerization systems are butadiene/styrene and styrene/acrylonitrile copolymer systems.

Generally, it is preferred that such polymers contain and are prepared by copolymerizng the $\alpha$-methyl-p-bromo-styrene of this invention in an amount in the range of about 5 to about 20 weight percent and, more preferably, about 10 to about 20 weight percent of the total polymerization monomers. However, with regard to copolymerizing with monomers containing phosphite or antimony, it is understood that there can be a synergistic effect resulting therefrom and that less amounts of the $\alpha$-methyl-p-bromo-styrene is needed to impart a satisfactory fire retardancy. In such cases, generally about 5 to about 15 or about 20 weight percent is satisfactory.

For example, in an aqueous emulsion polymerization situation, it may generally be desirable to provide an aqueous emulsion system which comprises on a monomer basis about 1 to about 50 weight percent α-methyl-p-bromo-styrene, about 1 to about 40 weight percent styrene and about 30 to about 90 weight percent butadiene or acrylonitrile, where the weight ratio of butadiene to acrylonitrile or styrene is in the range of about 1/1 to about 10/1. The reaction is then continued according to well-known emulsion polymerizng techniques to achieve a rubbery material which has improved flame retardancy in accordance with ASTM D-635-56T burning test.

The practice of this invention is further illustrated by reference to the following examples which are intended to be representative rather than restrictive of the scope of the invention. Unless otherwise indicated, all parts and percentages are by weight.

EXAMPLE I

Poly(α-methyl-styrene) was prepared by first charging to a reactor 2400 parts carbon tetrachloride as a solvent and 6 parts ferric chloride as a catalyst into a well stirred flask. The mixture was cooled to about 0°C and 1180 parts α-methyl-styrene was slowly added thereto on a drop-wise basis and at an even rate over a period of about 1 hour. After the addition of α-methyl-styrene the reaction temperature was maintained at about 0°C for an additional half hour in order to complete the reaction. The poly(α-methyl-styrene) was recovered by fractionation to remove the volatiles therefrom. The non-volatile content of the viscous product was found to be about 33 percent of the mixture before fractionation which is almost 100 percent of the theoretical amount obtainable.

The poly(α-methyl-styrene) solution was heated to 55°C and 1760 parts bromine was slowly added dropwise beneath the surface at a moderate rate, in order to control foaming of the reaction, over a period of about 6 hours. During this time, a nitrogen purge was used to facilitate the removal of hydrogen-bromide which formed by the mixture of the polymerization reaction. Bromine vapor escape, promoted by the nitrogen purge was prevented by the use of a dry ice condenser. The mixture was contained for an additional hour at a temperature in the range of about 55° to about 60°C in order to complete the reaction.

The resulting poly(α-methyl-p-bromo-styrene) can now be isolated as a polymer or the solution can be used as it is in its present form. Isolation of the polymer in this case was accomplished by precipitating the polymer from its carbon tetrachloride solution with methanol, by filtering and drying the yellowish precipitate. The yield of polymer was 1840 parts which amounts to about 94 percent of the amount theoretically obtainable.

The polymer was depolymerized by first forming a 50 percent solution of the dry polymer with 3900 parts of carbon tetrachloride. The solution was slowly added dropwise over a period of about 2 hours to a flask which was a part of a vacuum distillation apparatus. The temperature of the flask was adjusted to about 330° to about 360°C at a reduced pressure of about 2 to about 5 millimeters of mercury. Almost instant depolymerization occurred as each drop was added. At the end of the addition, about 150 parts of a brittle charred residue remained in the flask. The depolymerized polymer was recovered as the distillate. To the distillate was added 45 parts magnesium oxide to destroy any residual Lewis acid which might repolymerize the newly obtained monomer cationically during the ensuing distillation. The distillate was then redistilled by fractional distillation to obtain a distillate having a boiling point of about 80° to about 90°C at a reduced pressure of about 5 to 20 millimeters mercury. The distilled product had the following analysis shown in Table 1.

TABLE 1

| | |
|---|---|
| Purity | 99–100 percent (by gas chromatography) |
| Boiling Point | 81°C at 7 millimeter mercury pressure |
| Density | 1.345 at 25°C |
| Refractive Index | 1.579 at 25°C |
| Melting Point | 15°C |

The infrared analysis in combination with the properties shown in Table 1 confirmed that the α-methyl-p-bromo-styrene monomer had been obtained.

EXAMPLE II

Aqueous emulsion copolymerizations were conducted with the α-methyl-p-bromo-styrene obtained according to Example I. In one recipe, a 30/35/30 weight ratio of styrene/acrylonitrile/α-methyl-p-bromo-styrene monomer system was emulsion polymerized at a temperature in the range of about 50° to about 55°C. In a second recipe, a monomer system comprised 67/33 weight amounts of butadiene/α-methyl-p-bromo-styrene monomer system emulsion copolymerized at a temperature in the range of about 50° to about 55°C.

The recipe for several aqueous emulsion polymerizations is more clearly shown in the following Table 2.

TABLE 2

| | A | B | C |
|---|---|---|---|
| Water | 165 | 165 | 165 |
| Emulsifiers | 5 | 5 | 5 |
| Potassium persulfate | 0.5 | 0.5 | 0.5 |
| Styrene | 35 | 35 | 25 |
| α-methyl-styrene | 35 | 0 | 0 |
| α-methyl-p-bromo-styrene | 0 | 35 | 50 |
| Acrylonitrile | 30 | 30 | 25 |
| Mercaptan | 0.5 | 0.5 | 0.5 |
| Shortstop | 0.05 | 0.05 | 0.05 |
| Temperature (°F) | 100 | 100 | 100 |
| % Solids | | | |
| 4 hours | 2 | 6.6 | 15 |
| 8 hours | 5.8 | 21.6 | 30.9 |
| 12 hours | 25.6 | 36.7 | 34.6 |
| 16 hours | 35.3 | | 36 |

The resulting emulsion copolymers were tested for flame retardancy and showed substantially improved results in accordance with ASTM D-635-56T. The favorable flame retardant results are more clearly shown in the following Table 3.

TABLE 3

| Burn rate | .88"/min | self-extinguishing | self-extinguishing |
|---|---|---|---|
| Seconds burning time after ignition | | 13.3 | 2 |

Thus, this example demonstrates that the α-methyl-p-bromo-styrene substantially enhances the flame retardancy of the styrene/acrylonitrile copolymer by causing it to be self-extinguishing as compared to simply using an α-methyl-styrene which demonstrated a burn rate of 0.88 inch per minute. Furthermore, it should be pointed out that the α-methyl-p-bromo-styrene of this invention demonstrated a more favorable and controllable reaction rate. Namely, the α-methyl-p-bromo-styrene demonstrated a reaction rate which wascontrollably faster than α-methyl-styrene, and therefore a more useful monomer for the purpose of copolymerization.

In the practice of this invention, poly(α-methyl-styrene) can be brominated as a solvent solution, utilizing an inert solvent which is essentially non-reactive in the polymerization system. Particularly preferred are liquid chlorinated aliphatic hydrocarbons containing 1 to 2 carbon atoms. Representative of such chlorinated hydrocarbons are carbon tetrachloride, chloroform, methylene chloride, dichloro ethane, trichloro ethane and tetrachloro ethane. Generally, carbon tetrachloride is preferred. In the preparation of the solution, various amounts of the α-methyl-styrene can be used. Generally, a solution containing about 10 to about 40 and even up to about 50 weight percent α-methyl-styrene is desired, depending primarily upon viscosity and solubility limitations relating to temperature used and the molecular weight of the α-methyl-styrene itself. In these examples, an α-methyl-styrene having a molecular weight in the range of about 1,000 to about 5,000 was used.

As described in these examples, the α-methyl-p-bromo-styrene can be used as a co-monomer for enhancing the flame retardancy of copolymers in accordance with ASTM Test No. D-635-56T. Similarly, the α-methyl-p-bromo-styrene of this invention can be suitably used to enhance the flame retardancy of polymers and copolymers earlier described in this specification through solution and emulsion copolymerizations.

In the bromination reaction used in this invention, the reaction rate can be enhanced by conducting the bromination in the presence of a Lewis acid. Representative of the various Lewis acids are ferric chloride, ferric bromide, aluminum chloride, aluminum bromide and zinc chloride. Typically, only very small amounts of such catalysts need to be present, when used, such as from about 0.05 weight percent to about 0.5 or 1 weight percent based on the α-methyl-styrene.

While certain representative embodiments and details have been shown for the purpose of illustrating the invention, it will be apparent to those skilled in this art that various changes and modifications may be made therein without departing from the spirit or scope of the invention.

What is claimed is:

1. A method of preparing α-methyl-p-bromo-styrene which comprises the sequential steps of obtaining a chlorinated aliphatic hydrocarbon solvent solution of poly(α-methyl-styrene) having a molecular weight in the range of about 1,000 to about 200,000; brominating said polymer with liquid or gaseous bromine at a temperature in the range of about 20° to about 100°C; and depolymerizing said brominated polymer by heating to a temperature in the range of about 250° to about 500°C.

2. The method of claim 1 where said brominated polymer is depolymerized at a reduced pressure of about 1 to about 500 millimeters of mercury.

3. The method of claim 1 where said brominated polymer is depolymerized to monomer at a temperature in the range of about 300° to about 400°C and the resulting depolymerized polymer is characterized by having a melting point of about 12° to about 18°C, a boiling point of about 80° to about 85°C at about 7 millimeters of mercury, a density of about 1.34 to about 1.35 at 25°C and a refractive index of about 1.579 to about 1.580 at 25°C.

4. The method of claim 1 which comprises the sequential steps of brominating said solvent solution of poly(α-methyl-styrene) and subsequently depolymerizing said brominated polymer while essentially simultaneously recovering the product as a distillate by heating said solution to a temperature in the range of about 250° to about 500°C at a reduced pressure of about 1 to about 500 millimeters of mercury, where said depolymerization is conducted by essentially instantaneously heating said polymer solution to the required temperature range over a period of about 0.1 second to about 2 minutes.

5. The method of claim 4 where said chlorinated aliphatic hydrocarbon solvent is selected from carbon tetrachloride, chloroform, methylene chloride, dichloroethane, trichloroethane and tetrachloroethane, and where said bromination reaction rate is enhanced with a Lewis acid selected from ferric chloride, ferric bromide, aluminum chloride, aluminum bromide and zinc chloride.

* * * * *